(12) United States Patent
Hand et al.

(10) Patent No.: US 6,691,347 B2
(45) Date of Patent: Feb. 17, 2004

(54) HOSPITAL BED

(75) Inventors: Barry D. Hand, Mt. Pleasant, SC (US); Dana H. Delk, North Charleston, SC (US); Jack J. Brooks, Folly Beach, SC (US); Steven J. Doehler, Charleston, SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/335,468

(22) Filed: Dec. 31, 2002

(65) Prior Publication Data

US 2003/0115673 A1 Jun. 26, 2003

Related U.S. Application Data

(63) Continuation of application No. 09/944,558, filed on Aug. 31, 2001, now Pat. No. 6,499,160, which is a continuation of application No. 09/499,200, filed on Feb. 7, 2000, now Pat. No. 6,282,736, which is a continuation of application No. PCT/US98/16497, filed on Aug. 7, 1998.
(60) Provisional application No. 60/090,212, filed on Jun. 22, 1998, and provisional application No. 60/055,043, filed on Aug. 8, 1997.

(51) Int. Cl.[7] .............................................. A61G 7/008
(52) U.S. Cl. ................... 5/607; 5/609; 5/600
(58) Field of Search ..................... 5/600, 601, 607, 5/608, 609, 610, 611, 629

(56) References Cited

U.S. PATENT DOCUMENTS

| | | | |
|---|---|---|---|
| 1,021,335 A | 3/1912 | Robinson | 5/607 |
| 1,573,571 A | 2/1926 | Pohl | 378/179 |
| 1,667,982 A | 5/1928 | Pearson | 5/608 |
| 1,799,692 A | 4/1931 | Knott | 5/607 |
| 2,076,675 A | 4/1937 | Sharp | 5/609 |
| 2,239,821 A | 4/1941 | Knox | 5/607 |
| 2,311,542 A | 2/1943 | Holme | 5/609 |
| 2,417,378 A | 3/1947 | Robinson | 5/627 |
| 2,499,101 A | 2/1950 | Kluglein | 5/607 |
| 2,607,103 A | 8/1952 | Davidson | 27/28 |
| 2,613,371 A | 10/1952 | Keyes, Jr. | 5/607 |
| 2,639,206 A | 5/1953 | Butler | 5/621 |
| 2,667,169 A | 1/1954 | Kambourakis | 607/95 |
| 2,673,987 A | 4/1954 | Upshaw et al. | 5/86.1 |
| 2,803,022 A | 8/1957 | Wynkoop | 5/632 |
| 2,880,720 A | 4/1959 | Houghtaling | 601/90 |
| 2,902,701 A | 9/1959 | Driskill | 5/607 |
| 3,049,726 A | 8/1962 | Getz | 5/86.1 |

(List continued on next page.)

FOREIGN PATENT DOCUMENTS

| | | |
|---|---|---|
| EP | 0025701 | 3/1981 |
| EP | 0 569 308 A1 | 11/1993 |
| FR | 2 034 679 | 12/1970 |
| FR | 2 247 194 | 5/1975 |
| FR | 2 549 366 | 1/1985 |
| FR | 2 585 240 | 1/1987 |
| FR | 2 749 503 | 12/1997 |
| TW | 77886 | 11/1975 |
| WO | WO 93/05745 | 4/1993 |
| WO | WO 97/22323 | 6/1997 |
| WO | WO 98/39996 | 9/1998 |
| WO | WO 99/07320 | 2/1999 |
| WO | WO 99/53997 | 10/1999 |
| WO | WO 00/00117 | 1/2000 |
| WO | WO 00/00152 | * 1/2000 .................... 5/607 |

*Primary Examiner*—Robert G. Santos
(74) *Attorney, Agent, or Firm*—Bose McKinney & Evans LLP

(57) ABSTRACT

A patient support apparatus including a first patient support configured to be rotated about a longitudinal axis. The first patient support illustratively includes an inflatable bladder. A backboard may be removably coupled to the patient support apparatus and is configured to facilitate transport of a patient to and from the patient support apparatus.

50 Claims, 13 Drawing Sheets

U.S. PATENT DOCUMENTS

| | | | |
|---|---|---|---|
| 3,110,912 A | 11/1963 | Propst | 5/628 |
| 3,200,416 A | 8/1965 | Warrick | 5/608 |
| 3,206,188 A | 9/1965 | Douglass, Jr. | 5/614 |
| 3,226,734 A | 1/1966 | Coventon | 5/607 |
| 3,238,539 A | 3/1966 | Koch | 5/607 |
| 3,286,707 A | 11/1966 | Shafer | 601/5 |
| 3,302,218 A | 2/1967 | Stryker | 5/607 |
| 3,344,445 A | 10/1967 | Crawford | 5/430 |
| 3,388,700 A | 6/1968 | Mountz | 601/5 |
| 3,434,165 A | 3/1969 | Keane | 5/608 |
| 3,451,070 A | 6/1969 | Danielson | 5/83.1 |
| 3,499,529 A | 3/1970 | Katzfey et al. | 5/617 |
| 3,584,321 A | 6/1971 | Buchanan | 5/601 |
| 3,653,079 A | 4/1972 | Bourgraf et al. | 5/607 |
| 3,658,052 A | 4/1972 | Alter | 600/534 |
| 3,667,075 A | 6/1972 | Ballard et al. | 5/722 |
| 3,737,924 A | 6/1973 | Davis | 5/108 |
| 3,739,406 A | 6/1973 | Koetter | 5/608 |
| 3,748,666 A | 7/1973 | Seng | 5/609 |
| 3,752,153 A | 8/1973 | Copeland | 601/5 |
| 3,765,406 A | 10/1973 | Toole et al. | 601/5 |
| 3,783,863 A | 1/1974 | Kliever | 128/847 |
| 3,814,414 A | 6/1974 | Chapa | 5/601 |
| 3,820,176 A | 6/1974 | Feiertag | 5/611 |
| 3,827,089 A | 8/1974 | Grow | 5/607 |
| 3,828,377 A | 8/1974 | Eary, Sr. | 5/632 |
| 3,832,742 A | 9/1974 | Stryker | 5/610 |
| 3,851,644 A | 12/1974 | Slagle | 128/847 |
| 3,868,103 A | 2/1975 | Pageot et al. | 5/614 |
| 3,874,010 A | 4/1975 | Geary | 5/610 |
| 3,884,225 A | 5/1975 | Witter | 5/630 |
| 3,902,204 A | 9/1975 | Lee | 5/86.1 |
| 3,905,591 A | 9/1975 | Schorr et al. | 5/601 |
| 3,940,808 A | 3/1976 | Petrini | 5/83.1 |
| 3,941,365 A | 3/1976 | Frymoyer | 5/610 |
| 4,054,960 A | 10/1977 | Pettit et al. | 5/631 |
| 4,071,916 A | 2/1978 | Nelson | 5/658 |
| 4,080,673 A | 3/1978 | Weisler | 5/658 |
| 4,084,274 A | 4/1978 | Willis et al. | 5/609 |
| 4,109,329 A | 8/1978 | Tupper | 5/607 |
| 4,152,795 A | 5/1979 | Rodosta et al. | 5/658 |
| 4,156,815 A | 5/1979 | Hogan | 5/601 |
| 4,175,550 A | 11/1979 | Leininger et al. | 601/5 |
| 4,183,110 A | 1/1980 | Kidd et al. | 5/629 |
| 4,195,829 A | 4/1980 | Reser | 5/614 |
| 4,244,358 A | 1/1981 | Pyers | 606/242 |
| 4,274,167 A | 6/1981 | Immel | 5/610 |
| 4,277,857 A | 7/1981 | Svehaug | 5/610 |
| 4,356,577 A | 11/1982 | Taylor et al. | 5/608 |
| 4,384,378 A | 5/1983 | Getz et al. | 5/86.1 |
| 4,395,786 A | 8/1983 | Casey et al. | 5/616 |
| 4,432,353 A | 2/1984 | Vrzalik | 601/5 |
| 4,490,867 A | 1/1985 | Gabrielsson | 5/509.1 |
| 4,535,762 A | 8/1985 | Natchev | 606/244 |
| 4,557,471 A | 12/1985 | Pazzini | 5/618 |
| 4,558,857 A | 12/1985 | Heller | 5/618 |
| 4,572,493 A | 2/1986 | Hubert | 5/608 |
| 4,578,833 A | 4/1986 | Vrzalik | 5/607 |
| 4,584,989 A | 4/1986 | Stith | 600/18 |
| 4,586,492 A | 5/1986 | Manahan | 601/90 |
| 4,619,270 A | 10/1986 | Margolis et al. | 600/534 |
| 4,638,516 A | 1/1987 | Vrzalik | 5/611 |
| 4,655,206 A | 4/1987 | Moody | 5/628 |
| 4,658,450 A | 4/1987 | Thompson | 5/607 |
| 4,685,159 A | 8/1987 | Oetiker | 5/608 |
| 4,763,643 A | 8/1988 | Vrzalik | 601/93 |
| 4,769,584 A | 9/1988 | Irigoyen et al. | 318/648 |
| 4,827,541 A | 5/1989 | Vollman et al. | 5/613 |
| 4,841,585 A | 6/1989 | Masuzawa | 5/610 |
| 4,847,929 A | 7/1989 | Pupovic | 5/608 |
| 4,852,193 A | 8/1989 | Alsip et al. | 5/607 |
| 4,856,128 A | 8/1989 | Alsip et al. | 5/607 |
| 4,866,796 A | 9/1989 | Robinson et al. | 5/607 |
| 4,868,937 A | 9/1989 | Connolly | 5/608 |
| 4,872,657 A | 10/1989 | Lussi | 5/608 |
| 4,873,731 A | 10/1989 | Williamson | 5/615 |
| 4,895,173 A | 1/1990 | Brault et al. | 128/870 |
| 4,912,754 A | 3/1990 | Van Steenburg | 378/209 |
| 4,920,589 A | 5/1990 | LaVelle et al. | 5/607 |
| 4,924,537 A | 5/1990 | Alsip et al. | 5/608 |
| 4,937,901 A * | 7/1990 | Brennan | 5/607 |
| 4,939,801 A | 7/1990 | Schaal et al. | 5/607 |
| 4,941,221 A | 7/1990 | Kanzler | 5/615 |
| 4,944,054 A | 7/1990 | Bossert | 5/609 |
| 4,947,496 A | 8/1990 | Connolly | 5/607 |
| 4,958,817 A | 9/1990 | Heller et al. | 5/607 |
| 4,960,271 A | 10/1990 | Sebring | 5/608 |
| 4,987,622 A | 1/1991 | Shockey | 5/86.1 |
| 5,005,233 A | 4/1991 | Toivio et al. | 5/83.1 |
| 5,018,712 A | 5/1991 | Schaefer | 5/607 |
| 5,020,170 A | 6/1991 | Ruf | 5/607 |
| 5,023,968 A | 6/1991 | Diehl et al. | 5/81.1 R |
| 5,048,071 A | 9/1991 | Van Steenburg | 378/209 |
| 5,060,324 A | 10/1991 | Marinberg et al. | 5/81.1 T |
| 5,062,171 A | 11/1991 | Vrzalik | 5/713 |
| 5,088,706 A | 2/1992 | Jackson | 5/608 |
| 5,092,007 A | 3/1992 | Hasty | 5/715 |
| 5,103,511 A | 4/1992 | Sequin | 5/607 |
| 5,131,103 A | 7/1992 | Thomas et al. | 5/601 |
| 5,131,105 A | 7/1992 | Harrawood et al. | 5/607 |
| 5,131,106 A | 7/1992 | Jackson | 5/613 |
| 5,148,815 A | 9/1992 | Britton | 5/628 |
| 5,152,024 A | 10/1992 | Chrones et al. | 5/609 |
| 5,181,288 A | 1/1993 | Heaton et al. | 5/607 |
| 5,208,928 A | 5/1993 | Kuck et al. | 5/608 |
| 5,230,112 A | 7/1993 | Harrawood et al. | 5/607 |
| 5,230,113 A | 7/1993 | Foster et al. | 5/608 |
| 5,249,318 A | 10/1993 | Loadsman | 5/710 |
| 5,274,862 A | 1/1994 | Palmer, Jr. et al. | 5/81.1 R |
| 5,299,334 A | 4/1994 | Gonzalez | 5/607 |
| 5,319,817 A | 6/1994 | Hay et al. | 5/611 |
| 5,334,186 A | 8/1994 | Alexander | 604/180 |
| 5,345,630 A | 9/1994 | Healy | 5/708 |
| 5,398,356 A | 3/1995 | Pfleger | 5/608 |
| 5,404,603 A | 4/1995 | Fukai et al. | 5/609 |
| 5,412,823 A | 5/1995 | Sitta | 5/601 |
| 5,418,990 A | 5/1995 | Risasen | 5/608 |
| 5,427,338 A | 6/1995 | Garrett et al. | 248/68.1 |
| 5,435,323 A | 7/1995 | Rudy | 5/628 |
| 5,502,853 A | 4/1996 | Singleton et al. | 5/609 |
| 5,515,561 A | 5/1996 | Suggitt et al. | 5/607 |
| 5,515,869 A | 5/1996 | Powell et al. | 5/628 |
| 5,621,932 A | 4/1997 | Strachan | 5/600 |
| 5,621,933 A | 4/1997 | Knapp et al. | 5/608 |
| 5,664,270 A | 9/1997 | Bell et al. | 5/600 |
| 5,699,568 A | 12/1997 | Couldridge | 5/628 |
| 5,790,996 A | 8/1998 | Narfström | 5/610 |
| 5,860,899 A | 1/1999 | Rassman | 482/142 |
| 5,864,901 A | 2/1999 | Blumel | 5/610 |
| 5,966,762 A | 10/1999 | Wu | 5/710 |
| 6,065,165 A | 5/2000 | Delk et al. | 5/628 |
| 6,108,838 A | 8/2000 | Connolly et al. | 5/609 |
| 6,112,349 A | 9/2000 | Connolly | 5/607 |
| 6,119,292 A | 9/2000 | Haas | 5/715 |
| 6,240,584 B1 | 6/2001 | Perez et al. | 5/713 |
| 6,260,220 B1 | 7/2001 | Lamb et al. | 5/607 |
| 6,282,736 B1 * | 9/2001 | Hand et al. | 5/608 |
| 6,327,727 B1 | 12/2001 | Bocharnikov | 5/713 |
| 6,353,949 B1 | 3/2002 | Falbo | 5/610 |
| 6,385,801 B1 | 5/2002 | Watanabe et al. | 5/607 |
| 6,499,160 B2 * | 12/2002 | Hand et al. | 5/608 |

| | | | |
|---|---|---|---|
| 6,526,610 B1 * | 3/2003 | Hand et al. | 5/607 |
| 6,609,260 B2 * | 8/2003 | Hand et al. | 5/600 |
| 2002/0016994 A1 * | 2/2002 | Hand et al. | 5/600 |
| 2002/0026671 A1 | 3/2002 | Hand et al. | 5/608 |
| 2002/0138905 A1 * | 10/2002 | Bartlett et al. | 5/607 |
| 2002/0138906 A1 * | 10/2002 | Bartlett et al. | 5/609 |
| 2003/0115673 A1 * | 6/2003 | Hand et al. | 5/608 |
| 2003/0126683 A1 * | 7/2003 | Hand et al. | 5/607 |
| 2003/0140419 A1 * | 7/2003 | Bartlett et al. | 5/607 |
| 2003/0140420 A1 * | 7/2003 | Neiderkrom | 5/607 |
| 2003/0145382 A1 * | 8/2003 | Krywiczanin | 5/607 |

* cited by examiner

HOSPITAL BED

CROSS-REFERENCE TO RELATED APPLICATIONS

This application is a continuation of U.S. application Ser. No. 09/944,558, filed Aug. 31, 2001, now U.S. Pat. No. 6,499,160, which is a continuation of U.S. application Ser. No. 09/499,200, filed Feb. 7, 2000, now U.S. Pat. No. 6,282,736, which is a continuation PCT Application Serial No. PCT/US98/16497, filed Aug. 7, 1998, which claims the benefit of U.S. provisional application Serial No. 60/055,043 filed Aug. 8, 1997 and U.S. provisional application Serial No. 60/090,212 filed Jun. 22, 1998, all of which are expressly incorporated by reference herein.

BACKGROUND AND SUMMARY OF THE INVENTION

The present invention relates to a hospital bed. More particularly, the present invention relates to a proning bed which permits rotation of a patient supported on a patient support surface of the bed.

In an illustrative embodiment of the invention, a frame of the bed is operated to rotate the patient a full 360° about a longitudinal axis of a patient support assembly. In other words, the patient can be rotated 180° to prone the patient to aid with respiratory disorders such as Acute Respiratory Distress Syndrome (ARDS), or in order to perform surgical procedures or to permit the patient to lie face down on the support surface. The present invention permits full 180° rotation of a patient located on a patient support surface while providing spinal stability for spinal trauma patients.

The present invention illustratively provides a cantilevered design which cantilevers the entire patient support assembly from a foot end support assembly of the bed. No other support is required for rotation. The cantilevered design facilitates access to the head end of the bed which is substantially free from structural support. C-arm access is provided over the entire patient support surface for full body imaging.

According to an illustrative embodiment of the invention, a proning bed comprises a frame, a first support member coupled to the frame and configured to be located adjacent a posterior side of a patient, and a second support member coupled to the frame and configured to be located adjacent an anterior side of the patient. The proning bed further comprises a first patient support including an inflatable bladder, the first patient support being supported by the first support member and configured to support the patient in a supine position. A second patient support is supported by the second support member and is configured to support the patient in a prone position. The first support member and the second support member are configured to rotate the first patient support and the second patient support about a longitudinal axis.

Illustratively, a rotatable drive mechanism is operably coupled to the first support member and the second support member, the drive mechanism being configured to rotate the first patient support and the second patient support about the longitudinal axis. The drive mechanism is further configured to rotate the first patient support and the second patient support by at least 180° about the longitudinal axis.

Further illustratively, the second patient support includes an inflatable bladder. A controller is configured to selectively inflate and deflate the inflatable bladder of the first patient support and the inflatable bladder of the second patient support.

Illustratively, a fluid supply is in fluid communication with the inflatable bladder of the first patient support and is configured to inflate and deflate the bladder.

Further illustratively, the first support member comprises at least one pivotable door configured to provide access to the patient in a prone position, the inflatable bladder being coupled to the at least one pivotable door. The second support member comprises at least one pivotable door configured to provide access to the patient in a supine position.

Illustratively, a backboard is supported by the first support member, the backboard being removably coupled to the proning bed and configured to facilitate transport of the patient to and from the proning bed. The backboard includes at least one air bladder configured to provide a pressure reducing surface for the patient. A plurality of connectors are configured to mechanically couple the backboard to the proning bed.

According to another illustrative embodiment of the invention, a method for handling a patient on a proning bed is provided, the method including the step of providing a proning bed having a bed support, first and second support members, and first and second patient supports coupled to the first and second support members, at least one of the first and second patient supports including an inflatable portion, and the patient being supported by the first patient support in a supine position. The method further includes the steps of coupling the first support member to the bed support, coupling the second support member to the bed support, positioning a patient on the first patient support in a supine position, and inflating the inflatable portion. The method also includes the step of moving the first support member and the second support member so that the patient is supported by the second patient support in a prone position.

Illustratively, the first patient support includes an inflatable portion and the second patient support includes an inflatable portion. A fluid supply is configured to selectively inflate and deflate the inflatable portions of the first and second patient supports. The method further illustratively includes the step of inflating the inflatable portion of the second patient support before the first and second support members are moved.

Further illustratively, the step of inflating the inflatable portion comprises the step of inflating the inflatable portion of the first patient support. The method illustratively includes the further step of deflating the inflatable portion of the first patient support.

Illustratively, the step of inflating the inflatable portion comprises the step of inflating the inflatable portion of the first patient support before the first patient support is coupled to the bed support.

Illustratively, the method further includes the step of removing the first support member after the step of moving the first support member and the second support member.

Illustratively, the method further includes the steps of transporting the patient to the proning bed on a backboard, and removably coupling the backboard to the bed support.

In another illustrative embodiment of the invention, a therapy bed comprises a base, a frame coupled to the base, and a patient support assembly coupled to the frame and configured to be rotated about a longitudinal axis. The patient support assembly includes a backboard having a first patient support surface. The backboard is removably coupled to the frame to facilitate transport of the patient to and from the therapy bed.

Illustratively, the therapy bed further comprises a second patient support surface, the patient lying on the first patient support surface in a supine position, the first and second support surfaces configured to rotate by at least 180° about the longitudinal axis so that the patient is lying on the second patient support surface in a prone position.

Illustratively, the backboard includes an inflatable portion which is deflated when the patient is in the prone position. The second patient support surface includes an inflatable portion which is inflated when the patient is in the prone position. A fluid supply is configured to selectively inflate and deflate the inflatable portion of the backboard and the second support surface.

Further illustratively, the frame includes a rotatable drive mechanism coupled to the patient support assembly.

Illustratively, a plurality of connectors mechanically couple the backboard to the frame.

In a further illustrative embodiment of the invention, a method for handling a patient on a therapy bed is provided, the method including the steps of providing a backboard including a first patient support surface, positioning a patient on the first support surface in a supine position, and providing a therapy bed in spaced relation to the backboard, the therapy bed including a base and a frame coupled to the base. The method further includes the steps of transporting the backboard to the therapy bed, releasably coupling the backboard to the frame, and rotating the first patient support surface of the backboard about a longitudinal axis.

Illustratively, the method further includes the steps of providing a second patient support surface, coupling the second patient support surface to the frame, and simultaneously rotating the first patient support surface and the second patient support surface. The step of simultaneously rotating the first patient support surface and the second patient support surface comprises rotating the first patient support surface and the second patient support surface by at least 180° about the longitudinal axis.

Illustratively, the backboard includes an inflatable portion and the second patient support surface includes an inflatable portion.

Further illustratively, the method comprises the step of inflating the inflatable portion of the backboard before the rotating step. The method illustratively includes the further step of deflating the inflatable portion of the backboard.

Illustratively, the method includes the further step of inflating the inflatable portion of the second support surface.

Further illustratively, the therapy bed includes a fluid supply configured to selectively inflate and deflate the inflatable portion of the backboard and the inflatable portion of the second patient support surface.

Illustratively, the method further includes the step of removing the backboard from the therapy bed after the step of rotating the first patient support surface and the second patient support surface.

Further illustratively, the step of releasably coupling comprises the step of mechanically coupling the backboard to the frame through a plurality of connectors.

Additional objects, features, and advantages of the invention will become apparent to those skilled in the art upon consideration of the following detailed description of the illustrated embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
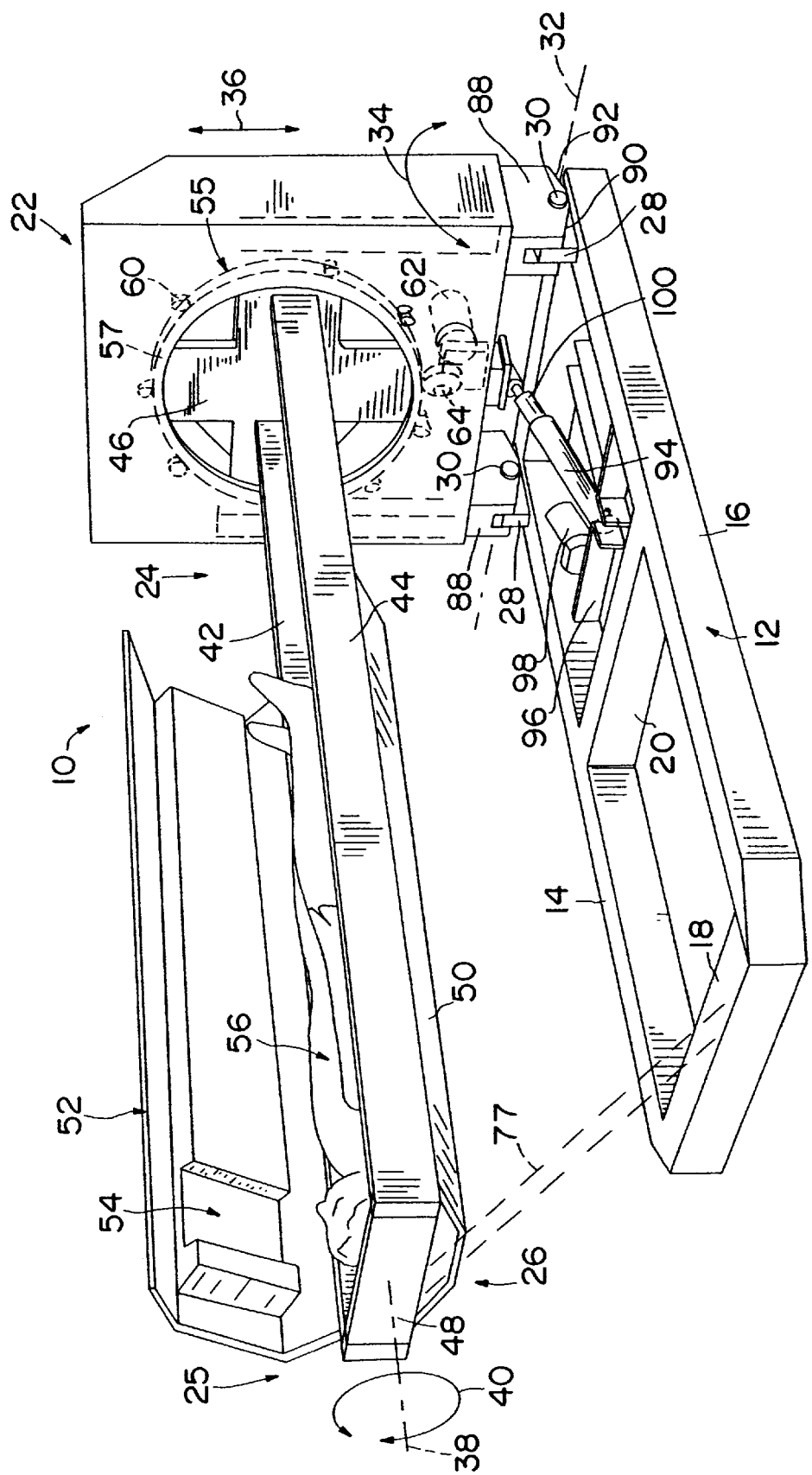
FIG. 1 is a perspective view illustrating a proning bed of the present invention.

Referring now to the drawings, FIG. 1 illustrates a bed 10 having a base 12 which includes opposite side members 14 and 16 and cross members 18 and 20 extending between side members 14 and 16. A support assembly 22 is located at a foot end 24 of bed 10. Support assembly 22 supports a patient support assembly 26 in a cantilevered fashion. Therefore, the head end 25 of bed 10 is open to facilitate access to the patient 56.

Support assembly 22 is pivotably coupled to pivot blocks 28 of base 12 by pivot connections 30. Therefore, support assembly 22 can pivot about axis 32 in the directions of double-headed arrow 34. As discussed in detail below, the support assembly 22 is movable up and down in the direction of double-headed arrow 36 to raise and lower the height of patient support assembly 26. Also as discussed below in detail, support assembly 22 can rotate the patient support assembly 26 about its longitudinal axis 38 as indicated by double-headed arrow 40. Support assembly 22 can rotate the patient support assembly 26 in either direction a full 360°.

Patient support assembly 26 includes a pair of horizontally extending arms 42 and 44 which are coupled to a cruciform-shaped plate 46 of support assembly 22. Arms 42 and 44 extend away from support assembly 22 in a cantilevered fashion. An end beam 46 extends between arms 42 and 44 at a distal end of patient support assembly 26. A patient support surface 50 is coupled between arms. When it is desired to rotate a patient, a proning support surface 52 is also coupled between arms 42 and 44. Proning support surface 52 includes a recess 54 for receiving the head of a patient 56. Support surfaces 50 and 52 are shown in an illustrative representation only. It is understood that support surfaces 50 and 52 will include selective placement of foam, air bladders, fluidized bladders, or other suitable support surfaces to reduce pressure on the patient 56 and/or support an unstable spine of the patient 56. The support surfaces 50 and 52 may include contoured support surfaces to minimize pressure on the patient. Layers of air and beads can be positioned over the contoured support surfaces. A vacuum can be selectively applied to the bead packs to further conform the support surfaces to the patient.

Figure 2:
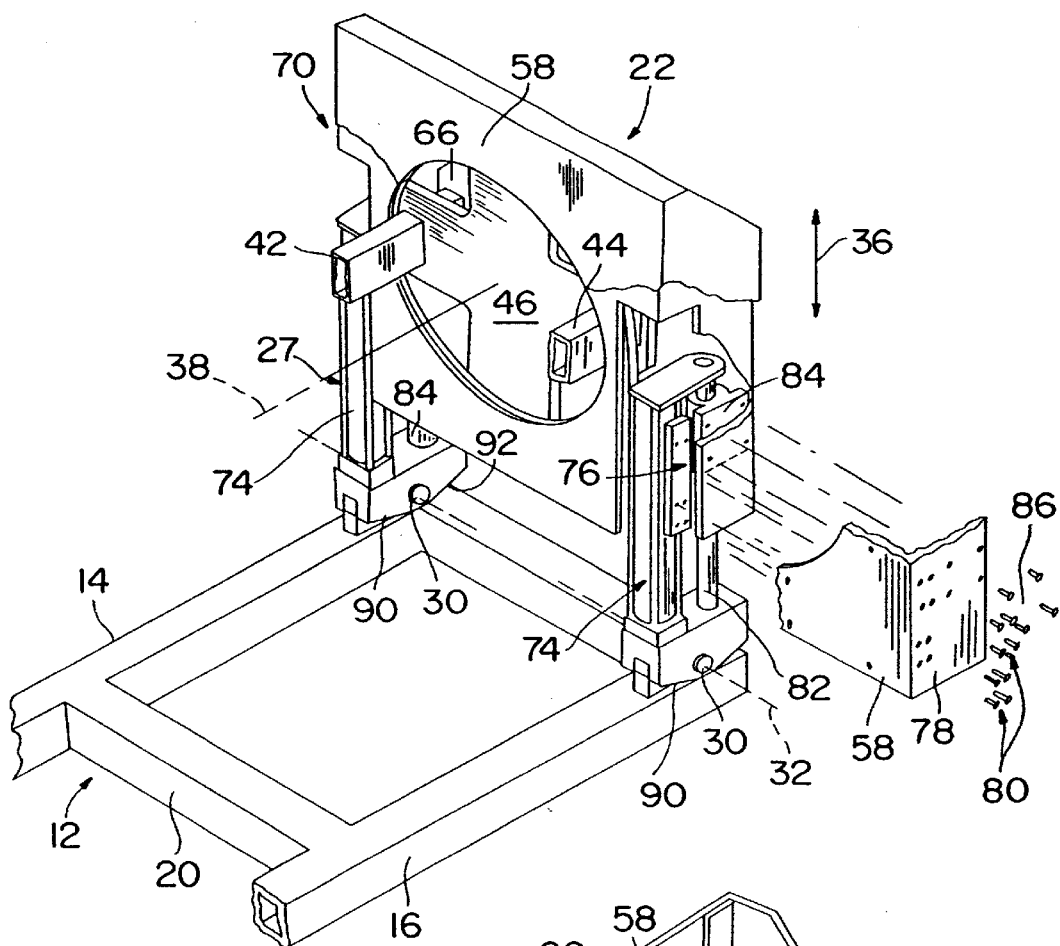
FIG. 2 is a perspective view, with portions broken away, illustrating a base and a patient support surface support assembly located at a foot end of the bed to control movement of the patient support surface.
Figure 3:
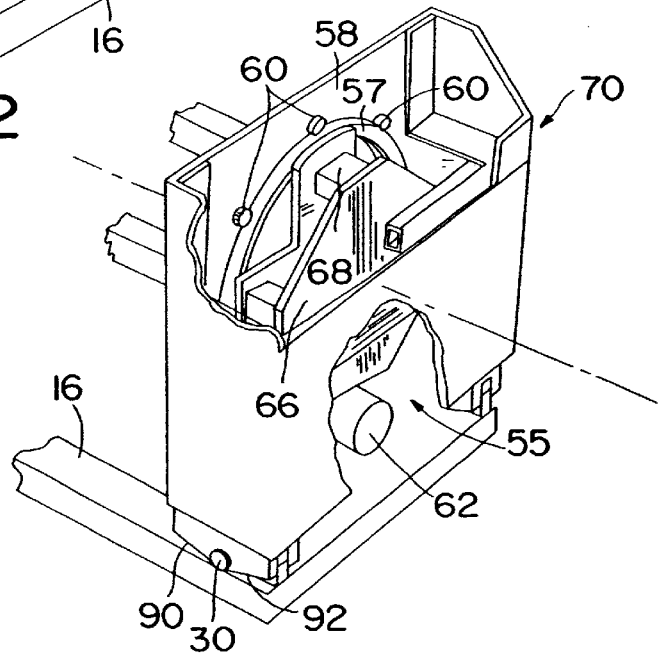
FIG. 3 is a perspective view, with portions broken away, illustrating additional details of the support assembly of the present invention.

Cruciform 46 is coupled to a drive mechanism 55 including rotatable, annular rack 57 which is held in place on a front surface 58 of support assembly 22 by rotatable bearings 60 which are coupled to front surface 58. Cruciform 46 includes four arms which are each secured to the annular rack 57. A motor 62 and gear 64 are located on support assembly 22. Gear 64 engages annular rack 57 to rotate the annular rack 57 relative to the front surface 58. Therefore, the support arms 42 and 44 coupled to the cruciform also rotate in the direction of double-headed arrow 40. As illustrated in FIGS. 2 and 3, the arms 42 and 44 extend through the cruciform 46 and are then welded to the cruciform 46. Arms 42 and 44 are also welded to a rear support plate 66. Extension sections 68 are welded between the support plate 66 and the cruciform 46 at locations between the support arms 42 and 44.

The support assembly 22 includes a movable frame 70 which is movable relative to outer supports 72. FIG. 2 illustrates the frame 70 in an upwardly extended position.

Opposite outer supports 72 each include a rodless cylinder 74 having a movable carriage 76. Movable carriage 76 is coupled to a sidewall 78 of movable frame 70 by fasteners 80. A guide cylinder 82 is located adjacent each rodless cylinder 74. A guide block 84 slides over each cylinder 82. Guide block 84 is coupled to sidewall 78 of frame 70 by fasteners 86.

Illustratively, rodless cylinders 74 are Lintra® rodless cylinder available from Norgren located in Rockford, Ill. An air supply is used to control movement of the carriages 76 on the rodless cylinders 74 to move the movable frame 70 of the support assembly 22 up and down in the directions of double-headed arrow 36. Since the annular rack 57, the cruciform 46 and the patient support assembly 26 are all coupled to the movable frame 70, the support surface 26 moves up and down in the direction of double-headed arrow 36 with the movable frame 70. Illustratively, the cylinders 74 provide and 8–9 inch lift. It is understood that hydraulics, lead screws, or other suitable lifting mechanisms can be used with the present invention.

The cantilevered design of the present invention advantageously suspends the patient support surface 26 from the support assembly 22. This permits full body C-arm access. In addition, a head end 25 of the bed is accessible for performing procedures on the patient 56. A support bar 77 can extend between the head end 25 of patient-support surface 26 and base 12 if desired. The support bar 77 can be moved into the support position engaging support surface assembly 26 while the patient 56 is on support surface 50. The support bar 77 can be removed from support surface assembly 26 for C-arm access or rotation.

Figure 4:
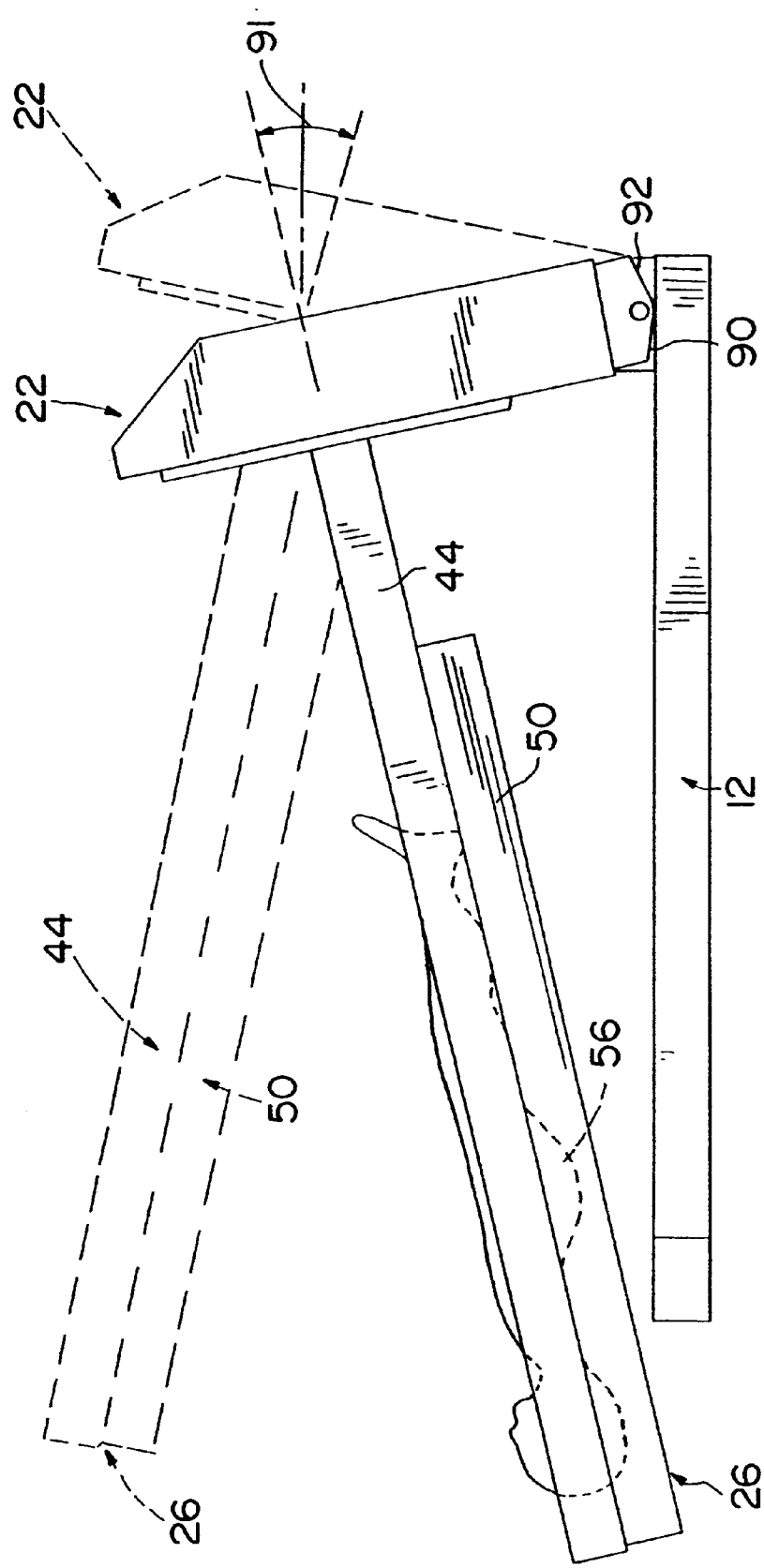
FIG. 4 is a side elevational view illustrating movement of the support assembly to position the patient support surface in either a Trendelenburg or a reverse Trendelenburg position.

The support assembly 22 is coupled to base 12 by blocks 88. Blocks 88 include a front angled stop 90 and a rear angled stop 92 which limit pivotable movement of the support assembly 22 relative to the base 12. As illustrated in FIG. 4, the support assembly 22 is pivotable relative to base 12 to move the patient support assembly 26 between a Trendelenburg position illustrated in solid lines in FIG. 4 to a reverse Trendelenburg position illustrated in dotted lines in FIG. 4. Illustratively, the pivotable movement is about +/−15° relative to horizontal in either direction as illustrated by angles 91 in FIG. 4. Front stop 90 engages base 12 when the patient support surface is in the Trendelenburg position shown in solid lines in FIG. 4. Second stop 92 engages the base 12 when the support assembly is in the reverse Trendelenburg position as shown in dotted lines in FIG. 4.

Pivotable movement of support assembly 22 about axis 32 is controlled by a cylinder 94 pivotably coupled to a cross member 96 which extends between arms 14 and 16 of base 12. A fluid source 98 is also coupled to cross member 96 to control movement of a piston 100 relative to cylinder 94 between an extended position and a retracted position. Piston 100 is pivotably coupled to support assembly 22. Therefore, retraction of piston 100 causes movement of the support assembly 22 forward to the Trendelenburg position. Extension of piston 100 causes pivotable movement of the support assembly 22 to the reverse Trendelenburg position.

Figure 5:
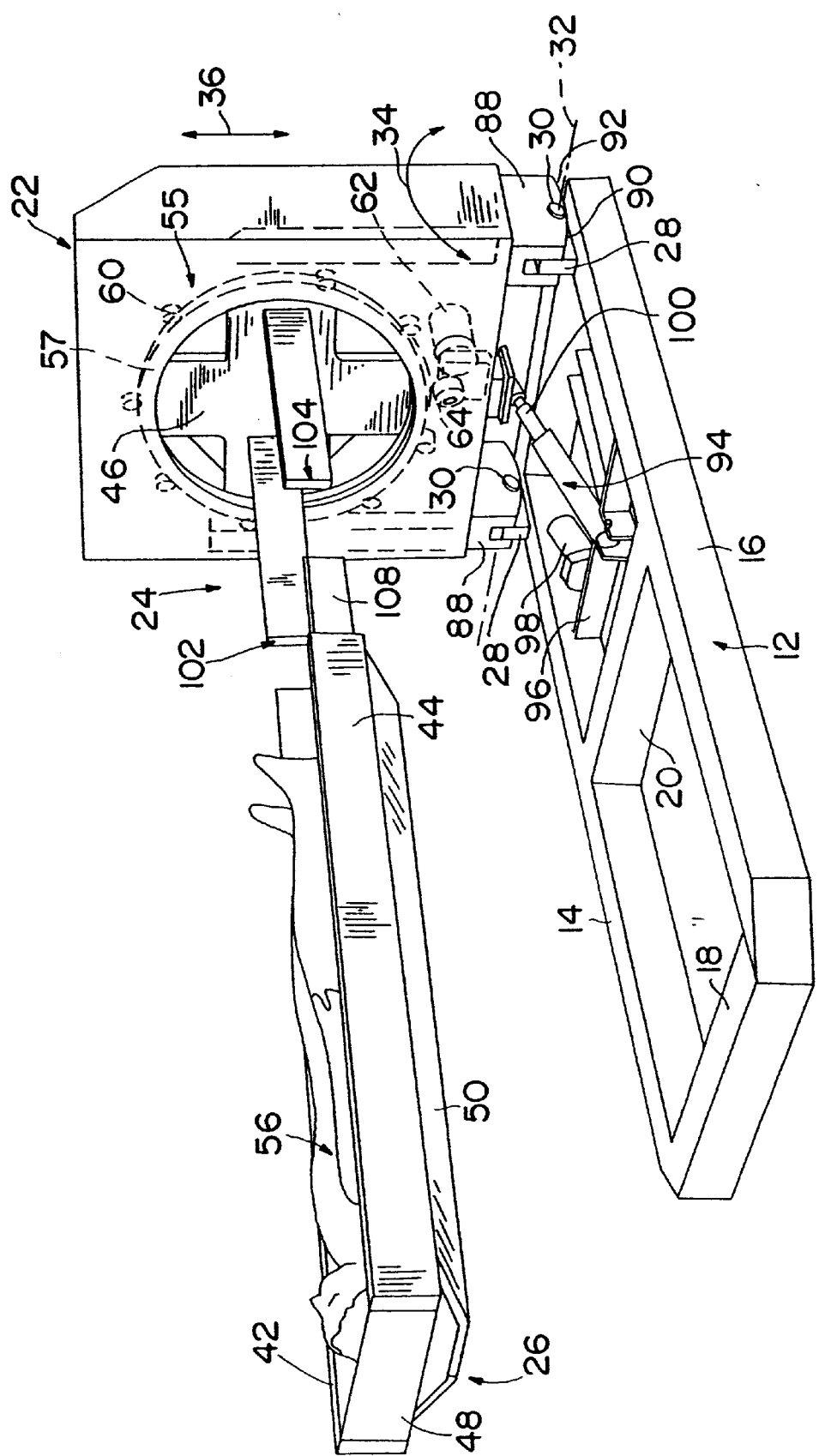
FIG. 5 is a perspective view illustrating another embodiment of the present invention in which a modular patient support assembly is configured to be coupled to receptacles on the support assembly.

Although the side arms 42 and 44 of the patient support assembly 26 are shown as solid arms in FIG. 1, it is understood that the side arms 42 and 44 may be shorter pieces cut off adjacent support assembly 22 as illustrated by arms 102 and 104 in FIG. 5. Since arms 102 and 104 are illustratively hollow receptacles, the remainder of the patient support assembly 26 includes arm extensions 106 and 108 which slide into the open ends of receptacle arms 102 and 104 extending from support assembly 22. Therefore, a patient could be transported directly from a trauma situation on the patient support surface 50 using suitable handles (not shown). The patient support assembly 26 and surface 50 may then be attached to the open ends of arms 102 and 104 and secured in position to form a cantilevered support surface 26 for the patient 56 without having to move the patient 56 from the support surface 50. Operation of the bed is then as described above.

The bed can be programmed to provide rotational therapy to the patient. The bed can also be used to prone the patient 56 so that the patient lies face down on the proning support surface 52.

In FIGS. 6–15, these elements referenced by numbers from FIGS. 1–5 perform the same or similar function. Patient support assembly includes a lower set of doors 110 and an upper set of doors 112. Lower set of doors 110 supports the patient support surface 50 for holding the patient in a supine position. Doors 110 and 112 are pivotably coupled to lifting apparatus 114 and 116. A first lifting apparatus 114 is coupled to arm 42, and a second lifting apparatus 116 is coupled to arm 44. Each lifting apparatus 114 and 116 includes an outer rectangular support 118 having a top surface 120 and a bottom surface 122. Each lifting apparatus 114, 116 further includes first and second lifting cylinder assemblies 124 and 126 located within side arms 42, 44, respectively. The first and second cylinder assemblies 124 and 126 each include a pair of cylinders 128, 130 which are coupled to arms 42, 44 by pivot connections 132 and 134, respectively. Cylinders 128 and 130 include pistons 136 and 138, respectively, which are pivotably coupled to top surface 120 of movable support 118 at locations 140. Illustratively, cylinders 128, 130 are hydraulic cylinders controlled by a suitable controller located within support assembly 22. Lines for controlling cylinders 128, 130 can be run through the arms 142, 144 to minimize line clutter.

Figure 6:
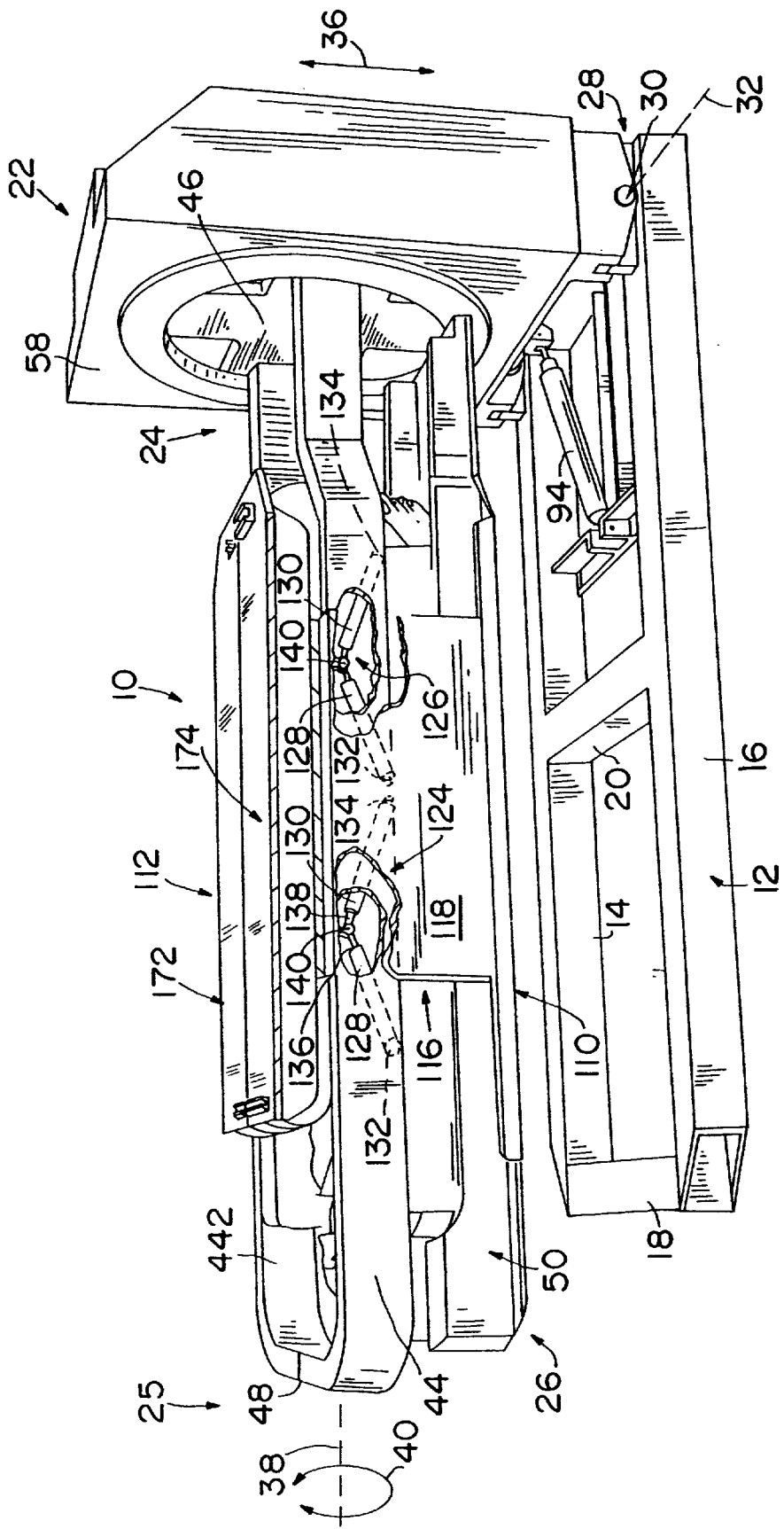
FIG. 6 is a perspective view illustrating a proning bed of the present invention, with a patient on a support surface in a supine position.
Figure 10:
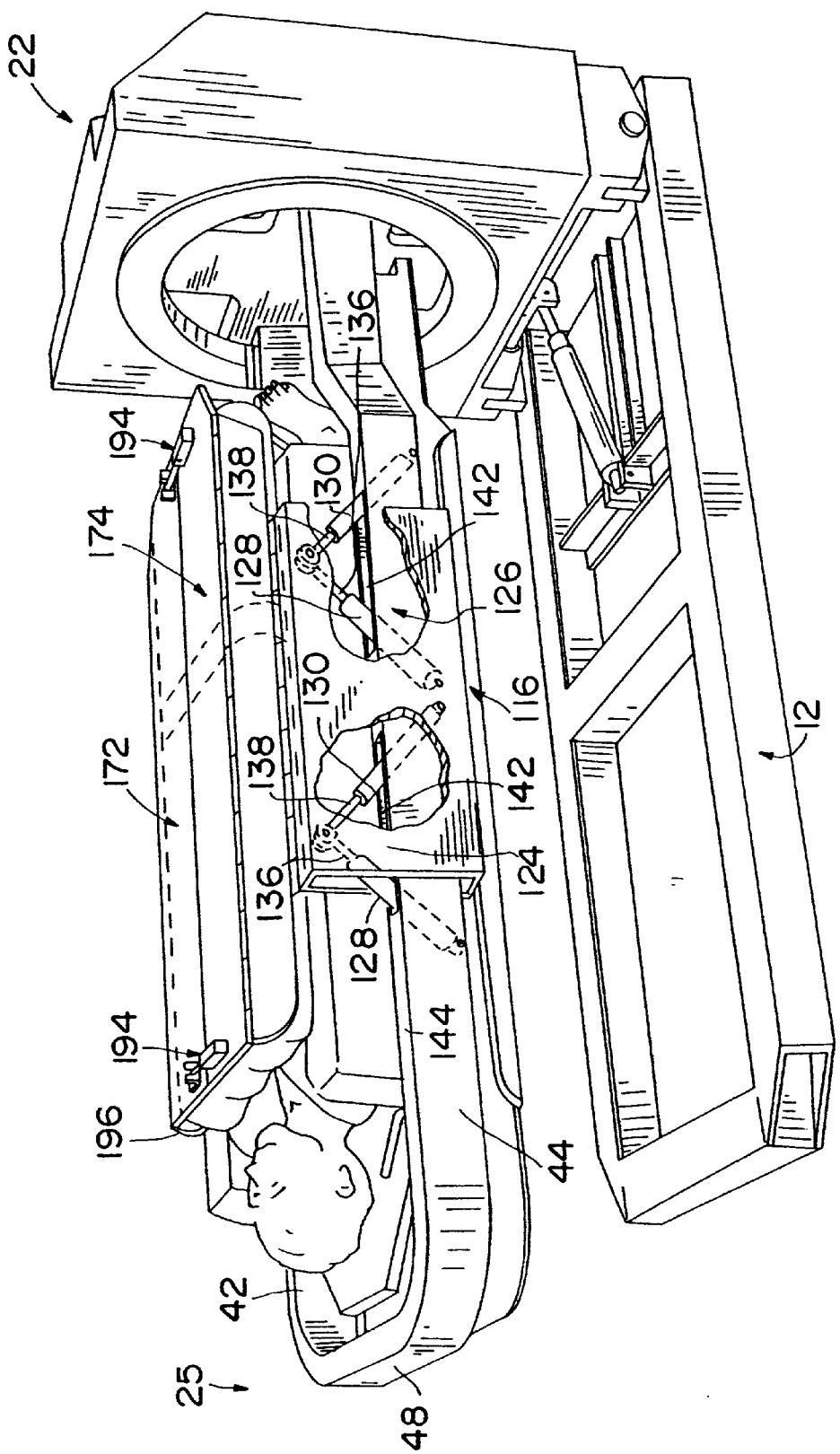
FIG. 10 is a perspective view similar to FIG. 6, illustrating the patient support surface in its raised position relative to the side arms of the bed.

The pistons 136, 138 are movable from a retracted position illustrated in FIG. 6 to an extended position illustrated in FIG. 10. In the retracted positions, pistons 136 and 138 position the support surface 50 at a lowermost position relative to arms 42 and 44 of the frame. In the extended position, the pistons 136 and 138 lift the movable support 118 and the patient support surface 50 coupled thereto upwardly to the position shown in FIG. 10. Arms 42 and 44 each are configured to include apertures 142 shown in FIG. 5 to permit the cylinders 128, 130 and pistons 136, 138 to move upwardly past a top surface 144 of frame arms 42, 44.

Figure 7:
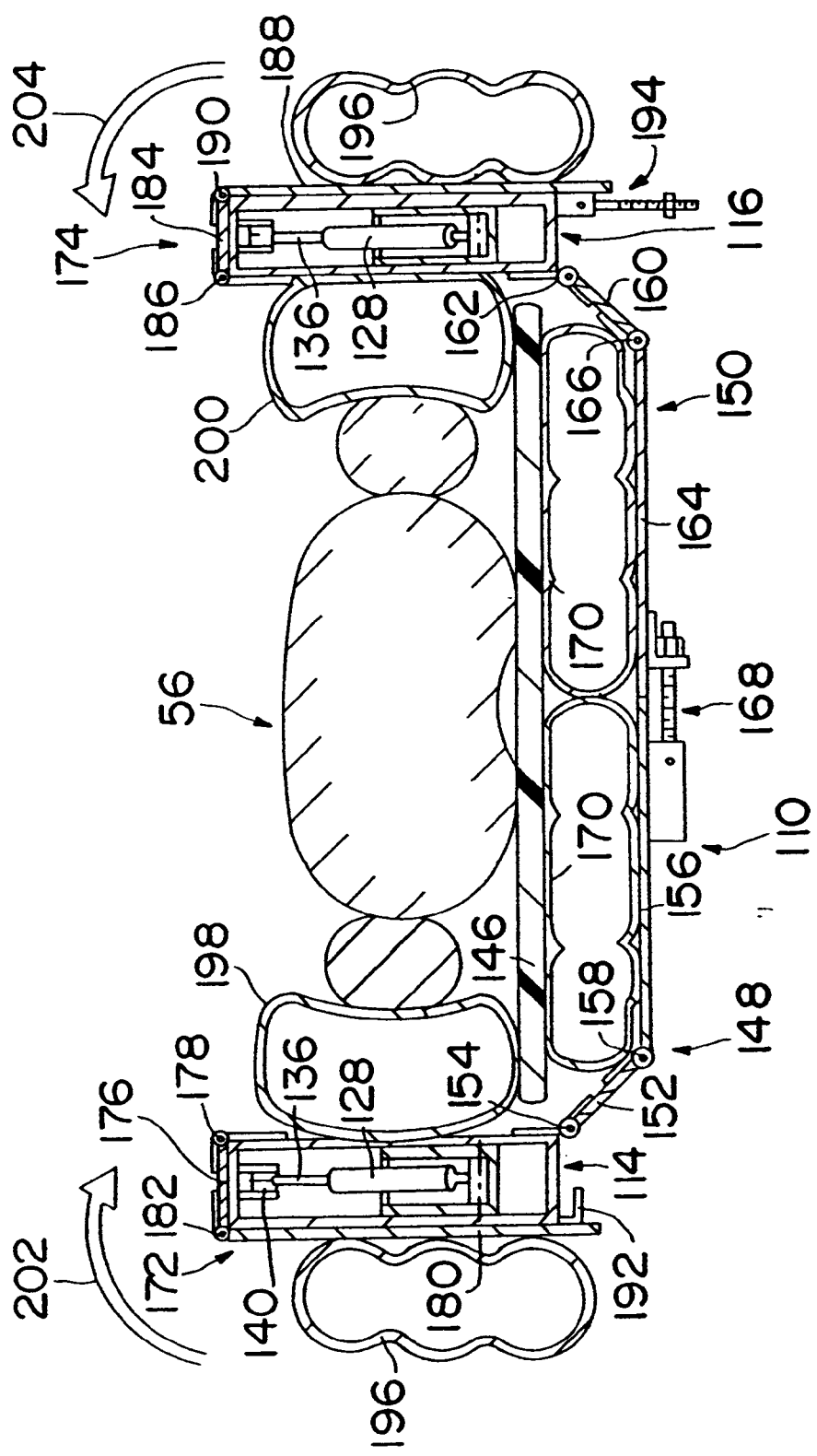
FIG. 7 is a sectional view taken through the patient support assembly of FIG. 1 illustrating top doors in an open position.

The bed 10 is configured so that a patient can be transported from a remote trauma location and positioned directly on the bed as illustrated in FIG. 7. Illustratively, the patient is transported to the bed 10 on a backboard 146. Illustratively, the backboard 146 may include air bladders, foam padding, and/or contoured sections to facilitate transport of the patient and to provide a pressure reducing surface when the backboard 146 is located on the bed 10. The backboard 146 may illustratively include a self-inflating surface, such as a Therm-A-Rest® mattress, for use in the field. When the backboard 146 is loaded into the bed 10, connectors are provided for coupling air bladders on the backboard to the air supply system and valves already located on the bed 10. Connectors are also provided for coupling the backboard 146 to the bed 10 mechanically and electrically.

As illustrated in FIG. 7, the bottom door assembly 110 includes a first door 148 pivotably coupled to the first lifting mechanism 114 and a second door 150 pivotably coupled to the second lifting mechanism 116. The first door 148 includes a first section 152 pivotably coupled to the first lifting mechanism 114 by hinge 154 and a second portion 156 pivotably coupled to the first portion 152 by hinge 158. Second door 150 includes a first portion 160 pivotably coupled to the second lifting mechanism 116 by hinge 162 and a second portion 164 pivotably coupled to the first portion 160 by hinge 166. Latches 168 are used to secure the first and second doors 148 and 150 in a closed position illustrated in FIG. 7 to provide a support for the backboard 146. Illustratively, a pair of air bladders 170 are located on an inner surface of doors 148 and 150 to provide a support for backboard 146. Alternatively, the patient can be situated directly on the air bladders 170 if the patient has not been transported to the bed on the backboard 146.

The proning doors 112 similarly include a first door 172 and a second door 174 shown in an open position in FIG. 7. Door 172 includes a first portion 176 pivotably coupled to first lifting apparatus 114 by hinge 178. Door 172 further includes a second portion 180 pivotably coupled to first portion 176 by hinge 182. Door 174 includes a first portion 184 coupled to second lifting apparatus 116 by hinge 186 and a second portion 188 pivotably coupled to first portion 184 by hinge 190. A first latch portion 192 is coupled to second door portion 180 of door 172, and a second latch portion 194 is coupled to second door portion 188 of second door 174. Air bladders 196 are also coupled to second door portions 180 and 188. FIG. 7 also illustrates a pair of inner inflatable side bladders 198 and 200 located along opposite sides of the patient 56.

FIG. 7 illustrates the top doors 172 and 174 in an open position. In the open position, first door portions 176 and 184 rest upon top surface 120 of the first and second lifting apparatus 114, 116, respectively. Therefore, the second door portions 180 and 188 can lie adjacent outer surfaces 118 of the first and second lifting apparatus 114 and 116, respectively, to conserve space. Air bladders 196 may be deflated to conserve additional space.

Figure 8:
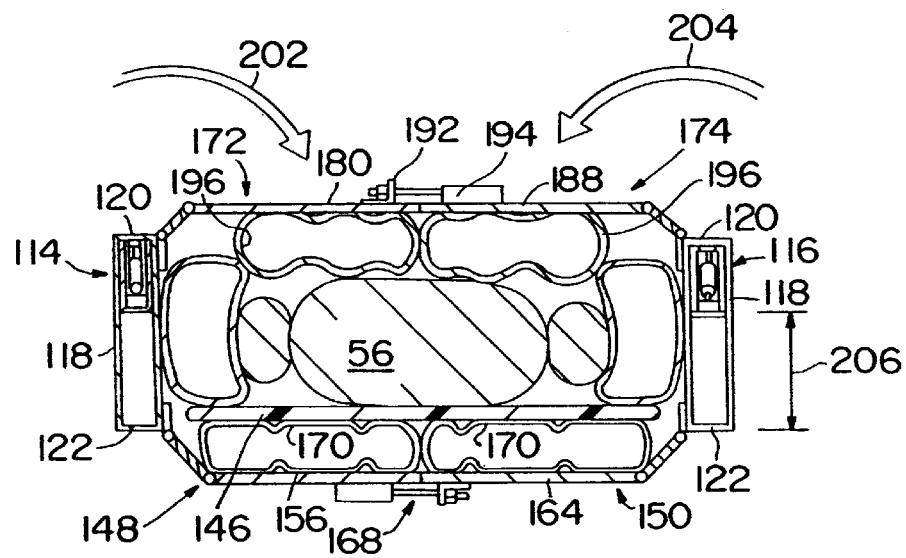
FIG. 8 is a sectional view through the patient support assembly of FIG. 6 with the proning doors in a closed and latched position and with a lifting apparatus on each side of the patient support surface, each lifting apparatus being adjusted to move the patient support surface to its lowermost position relative to support arms of the bed.

After the patient is transported to the bed 10 from an injury site or other location on backboard 146, the patient 56 and the backboard 146 are loaded into the bed 10 as illustrated in FIG. 7 with the patient in the supine position. If it is desired to prone the patient 56 for a medical procedure or therapy, the doors 172 and 174 are closed in the direction of arrows 202 and 204 of FIG. 7, respectively. Once the doors are moved to a closed position illustrated in FIG. 6 and 8–10, latches 192 and 194 are connected to secure the doors 172 and 174 together. It is understood that any type of latch mechanism can be used to hold the doors 172 and 174 in the closed position. As shown in FIG. 8, the air bladders 196 are configured to lie over the patient 56 when the doors 172 and 174 are closed.

In FIG. 8, the pistons 136 and 138 of cylinders 128 and 130, respectively, are in the retracted position shown in FIG. 6. Therefore, the arms 42 and 44 are located adjacent top surface 120 of support 118 of the first and second lifting apparatus 114 and 116. Therefore, bottom surfaces of arms 42 and 44 are spaced apart from a bottom surface 122 of first and second lifting apparatus 114 by a distance 206. In the position of FIGS. 6 and 8, the patient 56 is located at the lowermost support position relative to arms 42 and 44.

Figure 9:
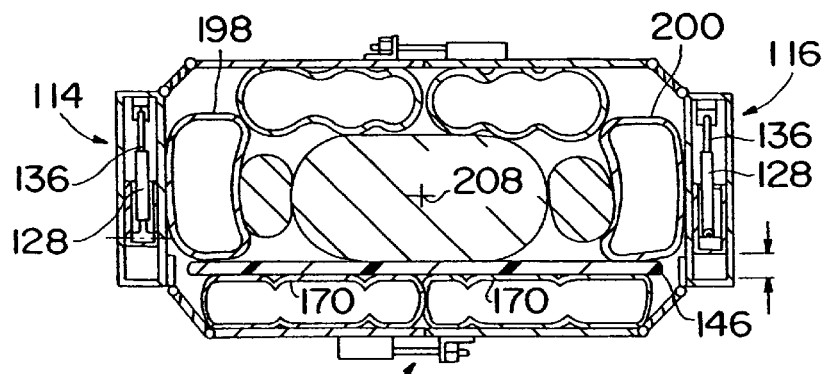
FIG. 9 is a sectional view similar to FIG. 8 in which the lifting apparatus are actuated to move a patient support surface upwardly relative to side support arms of the bed.
Figure 11:
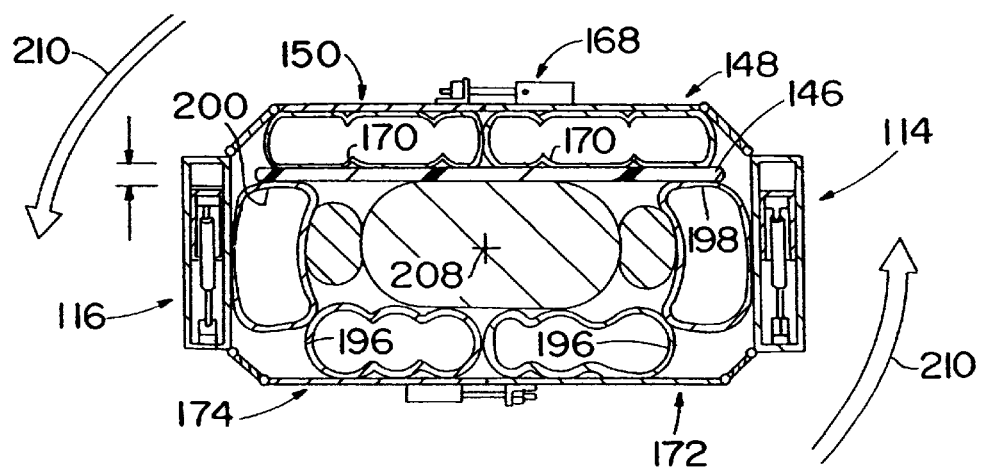
FIG. 11 is a sectional view taken through the patient support surface of FIG. 5, after the bed is operated to rotate the support surface, thereby turning the patient over to a prone position.

When it is desired to rotate or prone the patient, it is desirable to move the patient's center of gravity to a location above a pivot axis 138 of patient support assembly 26. Therefore, before rotating the patient 56, the first and second lifting apparatus 114 and 116 are actuated to extend the pistons 136 and 138 from cylinders 128 and 130 of the first and second cylinder arrangements 124 and 126. By extending the pistons 136 and 138, the top surfaces 120 of supports 118 of the lifting apparatus 114 and 116 move upwardly to the position illustrated in FIGS. 9 and 10. FIG. 9 shows that the distances between the bottom surfaces arms 42 and 44 is closer to the bottom surfaces 122 of supports 118 lifting apparatus 114 and 116 in the FIG. 9 configuration. The patients center of gravity 208 is at or slightly above the location of pivot axis 38. This positioning of patient 56 facilitates the rotating operation and provides less of a falling sensation for the patient 56 as rotation begins.

A controller of the present invention is configured to position the patient properly for proning automatically. A caregiver enters the patient's height and weight using an input device, and then the controller calculates a location of the center of gravity of the patient using known algorithms. The controller then sends appropriate control signals to the cylinders 128 and 130 to lift the patient a desired distance. Once the patient is positioned as illustrated in FIGS. 9 and 10, the controller actuates the drive motor and gear which drives the annular ring and rotates the cruciform 46 and arms 42 and 44 in the direction of arrows 210 in FIG. 11 until the patient has been proned. Once in the prone position of FIG. 11, latches 168 are opened to permit doors 148 and 150 to be moved away from the patient 56. Backboard 146 can then be removed to expose a back of the patient 56. Before the patient is moved to the prone position shown in FIG. 11, an appropriate head support member (not shown) is coupled to the proning doors 112 to support the patient's head and while in the prone position. Alternatively, the length of doors 172 and 174 may be extended and formed to include a recess for receiving the patient's face.

Figure 12:
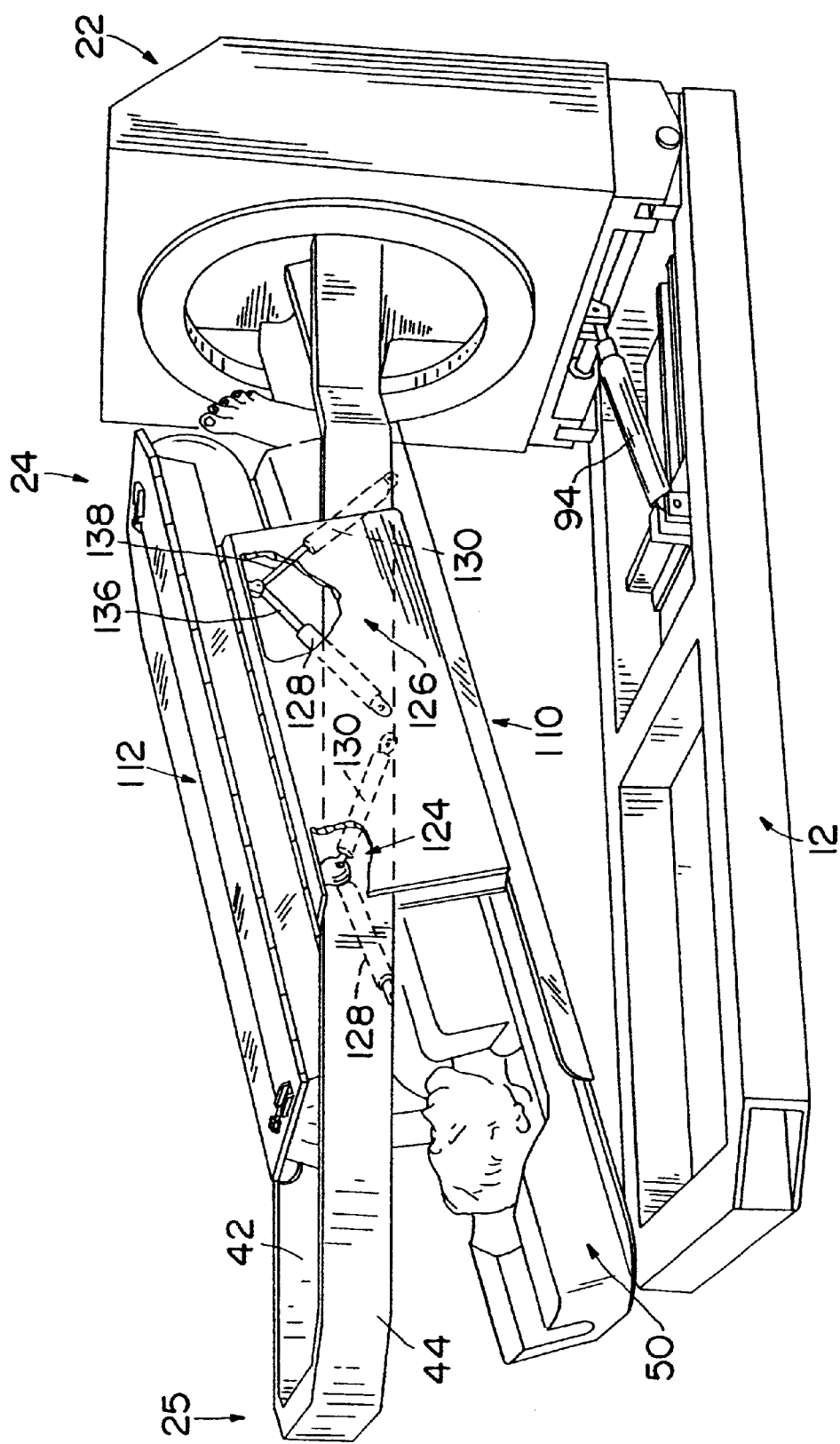
FIG. 12 is a perspective view illustrating the patient support surface of the bed moved to a Trendelenburg position.
Figure 13:
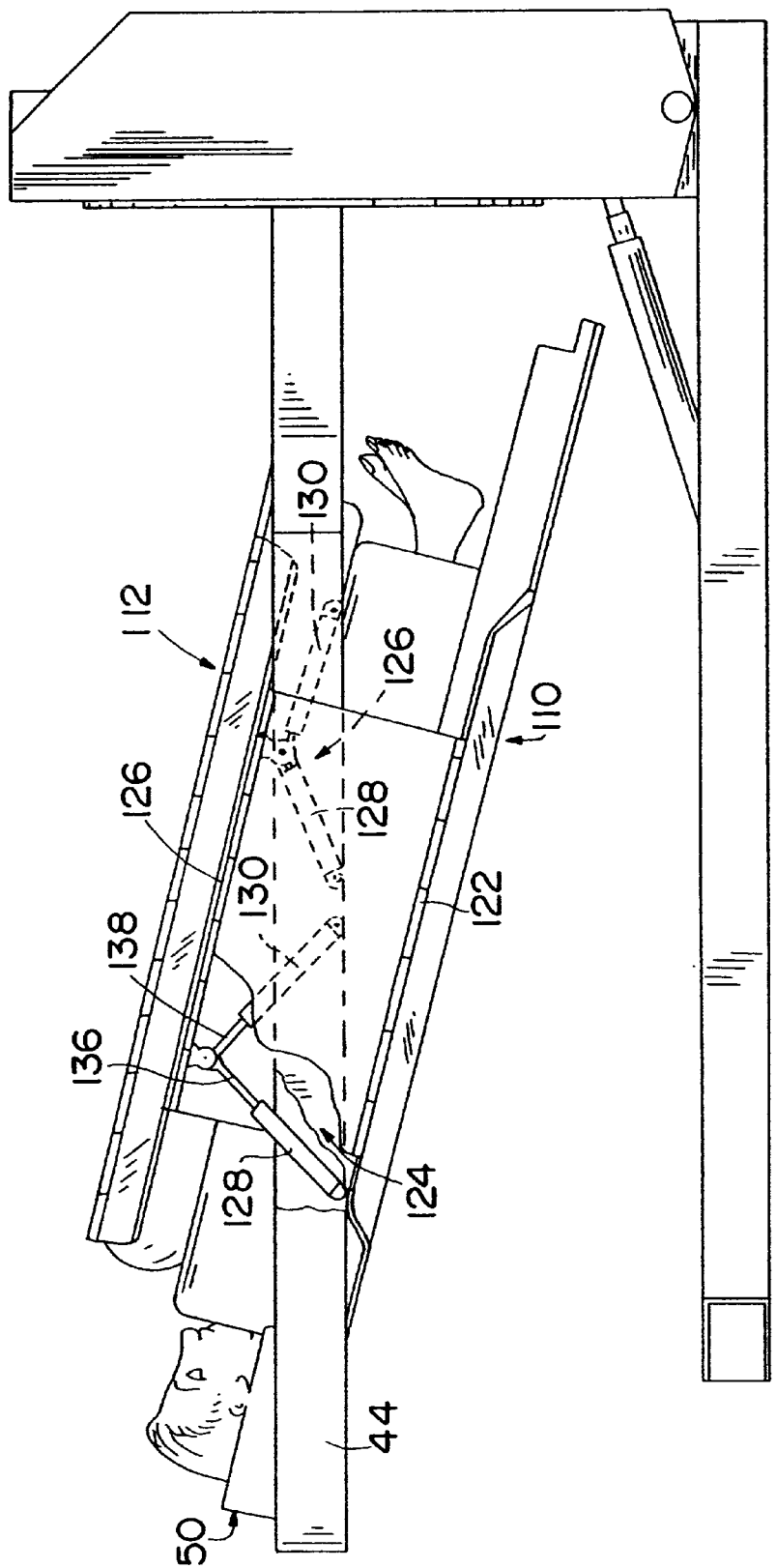
FIG. 13 is a perspective view of the bed of the present invention with the patient support surface in a reverse Trendelenburg position.

As shown in FIGS. 12 and 13, lifting apparatus 114, 116 may also be used for moving the patient support surface 50 from a Trendelenburg position shown in FIG. 12 to a reverse Trendelenburg position shown in FIG. 13. Using the first and second lifting apparatus 114, 116 in this manner eliminates the need for a separate cylinder 94 and a pivotable connection between support 22 and base 12. In other words, the support 22 may be rigidly coupled to base 12 when the first and second lifting apparatus 114 and 116 are used for the Trendelenburg and reverse Trendelenburg positioning.

As shown in FIG. 12, when the pistons 136 and 138 of the first pair of cylinders 124 are in the fully retracted position and the pistons 136 and 138 of the second set of cylinders 126 are in the fully extended position, the patient support surface 50 moves to a Trendelenburg position. Conversely, when the pistons 136 and 138 of the first set of cylinders 124 are moved to fully extended and the pistons 136, 138 and the second set of cylinders 126 are moved to the fully retracted position, the patient support 50 moves to a reverse Trendelenburg position as shown in FIG. 13.

Therefore, the lifting apparatus 114, 116, could also be used to provide rotation of patient 56 about a lateral axis perpendicular to longitudinal axis 38 and the patient 56. In other words, the lifting apparatus 114, 116 can be used to move the patient back and forth between the FIG. 12 position and the FIG. 13 position.

Figure 14:
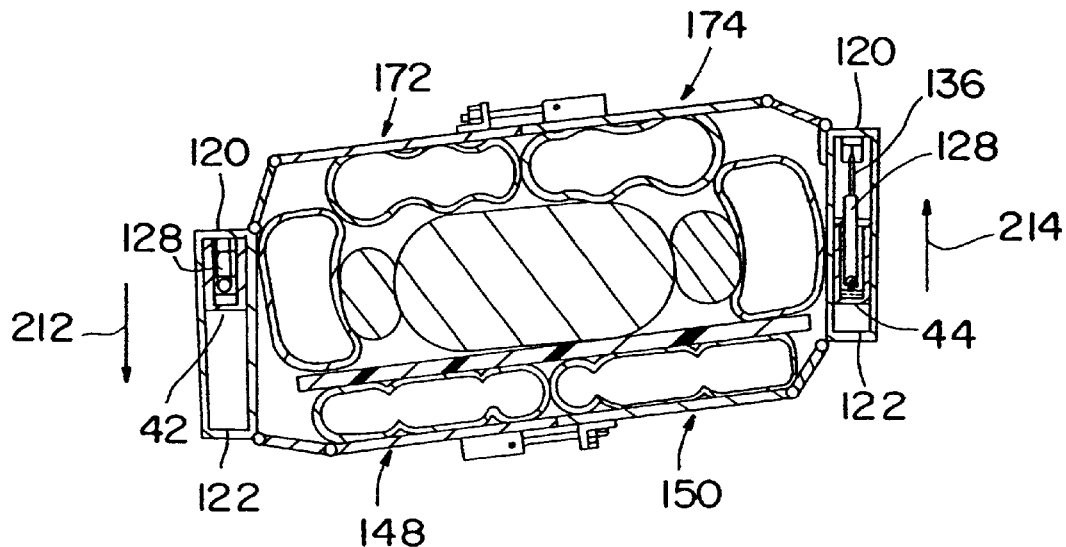
FIGS. 14 and 15 illustrate actuation of a lifting mechanisms on opposite sides of the bed for providing patient rotation using only the lifting mechanisms actuated in opposite, alternating directions.
Figure 15:
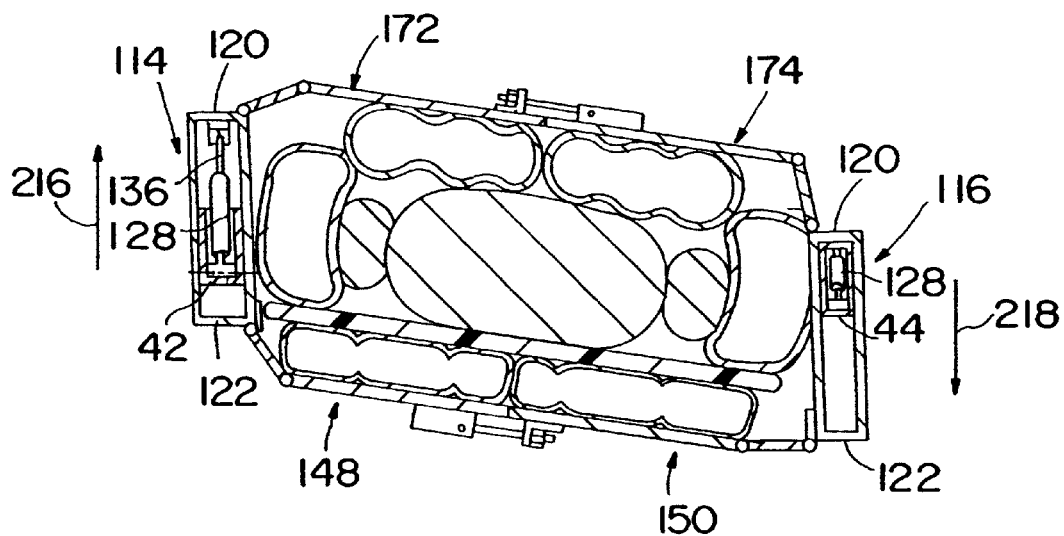

As shown in FIGS. 14 and 15, the first and second lifting apparatus 114, 116 may also be used to provide limited rotational therapy for the patient 56 about axis 38. The main drive motor within support assembly 22 can also be used for rotational therapy. In other words, the entire frame assembly 42, 44, and 46 may be rotated back and forth about axis 38 to provide rotational therapy for the patient. To provide the rotational therapy using only the first and second lifting apparatus 114, 116, the following sequence is used. The pistons 136 and 138 of the first and second cylinder pairs 124 and 126 in lifting apparatus 114 are moved to the retracted position while the pistons 136 and 138 of the cylinders 124 and 126 of lifting apparatus 116 are moved to the extended position as shown in FIG. 14. This causes the support 118 of first lifting apparatus 114 to move downwardly in the direction of arrow 212 and the support 118 of second lifting apparatus 116 to move upwardly in the direction of arrow 214. Next, the pistons 136 and 138 of the cylinder pairs 124 and 126 of lifting apparatus 114 are extended to move the support 118 of lifting apparatus 114 upwardly in the direction of arrow 216 of FIG. 15. Simultaneously, the pistons 136 and 138 of the cylinder pairs 124 and 126 of lifting apparatus 116 are retracted to move the support 118 of second lifting apparatus 116 downwardly in the direction of arrow 218. Therefore, as shown in FIGS. 14 and 15, rotational therapy can be provided to the patient 56 by alternately extending and retracting, in opposite timing, the pistons 136 and 138 of the cylinder pairs 124 and 126 of first and second lifting apparatus 114 and 116.

Figure 16:
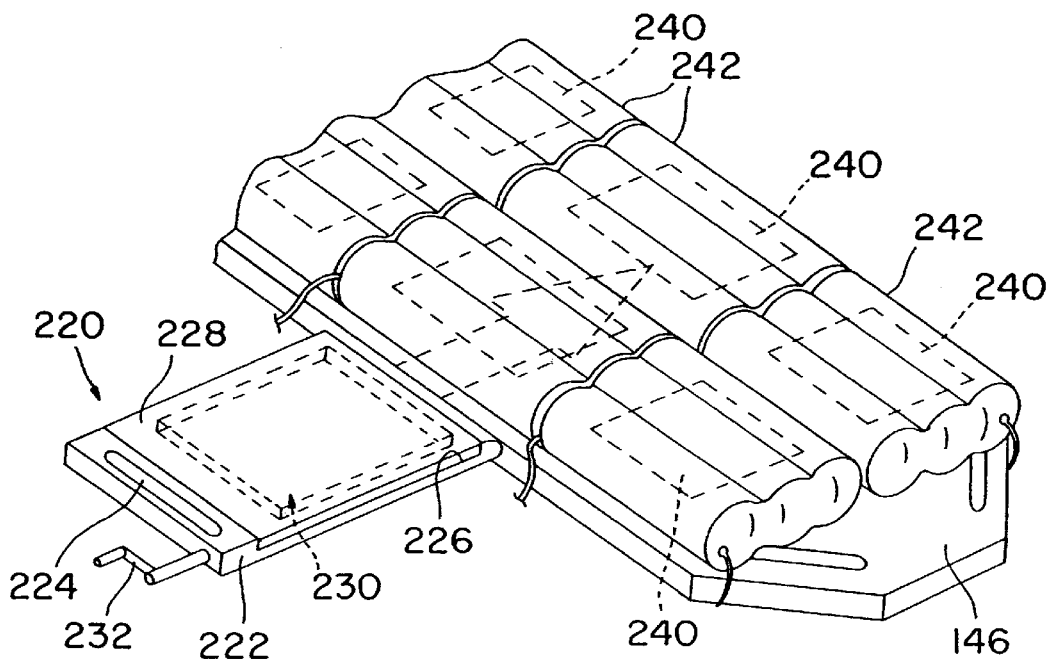
FIG. 16 illustrates insertion of an x-ray cassette below the patient support surface of the present invention.
Figure 17:
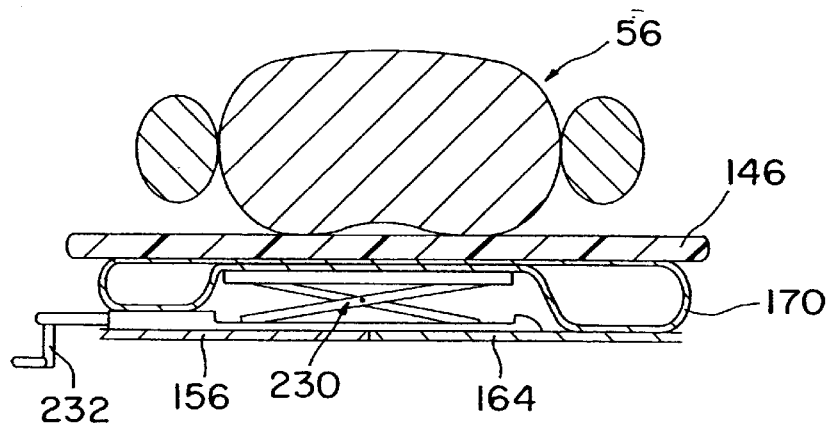
FIG. 17 is a sectional view illustrating actuation of the x-ray cassette holder to move the x-ray cassette close to a patient support surface to improve imaging.

FIGS. 16 and 17 illustrate an x-ray carriage 220 including a frame 222 having a handle 224 and a recessed portion 226 configured to receive an x-ray cassette 228. Carriage 220 also includes a lifting mechanism 230 best illustrated in FIG. 17 which is operated by a crank 232. The carriage 220 is designed to be inserted below bladders 170 and backboard 146 to lie on doors 156 and 164. Appropriate openings (not shown) are formed in door sections 152 or 160 to permit insertion of the carriage 220. Once the carriage 220 is positioned at a desired location, lifting apparatus 230 is actuated to lift the x-ray cassette 228 upwardly as shown in FIG. 17. The bladder 170 above the x-ray cassette 228 is deflated to permit the x-ray cassette 228 to be moved upwardly against a bottom surface of backboard 146. By moving the x-ray cassette 128 closer to the bottom surface of backboard 146, imaging is improved.

In another embodiment of the present invention, the apparatus includes surface pressure sensing integrated into the patient support surface. Specifically, an array of capacitive pressure sensors 240 are coupled to a top surface of patient support bladders 242 as shown in FIG. 16. Foam support surfaces may be located in the air bladders 242, if desired. As a patient 56 changes positions on the support bladders 242, or is rotated within the bed 10, pressure within each bladder 242 is adjusted based on inputs from the pressure sensor array 240 to keep interface pressure below capillary closure pressure or at as low a pressure as possible.

Figure 18:
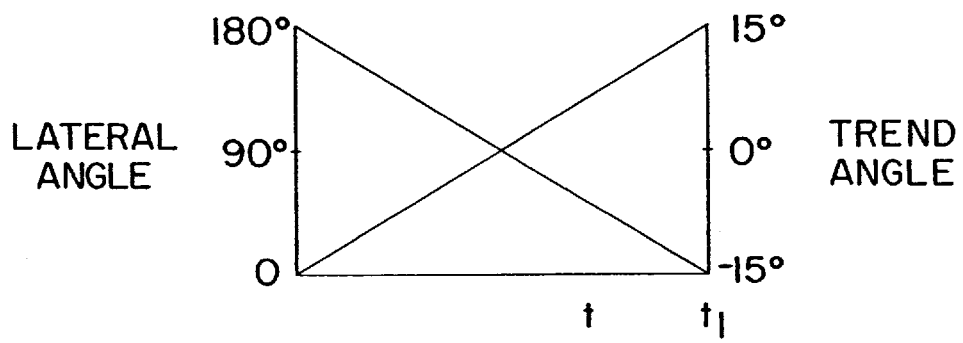
FIG. 18 is a chart illustrating rotation of the patient support surface about both a lateral axis and a longitudinal axis.

As discussed above, the bed of the present invention can be used to provide rotation about longitudinal axis 38 and about a lateral axis generally perpendicular to the longitudinal axis 38. The bed can move the patient about the longitudinal axis 38 up to 360°. At the same time, Trendelenburg angles of +/−15° are also possible. For instance, a patient requiring head elevation and proning can be in reverse Trendelenburg position shown in FIG. 13 while in the supine position. As the patient 56 is rotated to the prone position, the bed also actuates the lifting apparatus or tilting apparatus to move the patient support surface to the Trendelenburg position. Therefore, when the patient is in the prone position, the patient's head will still be elevated. A graph shown in FIG. 18 illustrates rotation angles about the lateral axis and longitudinal axis 38.

Figure 19:
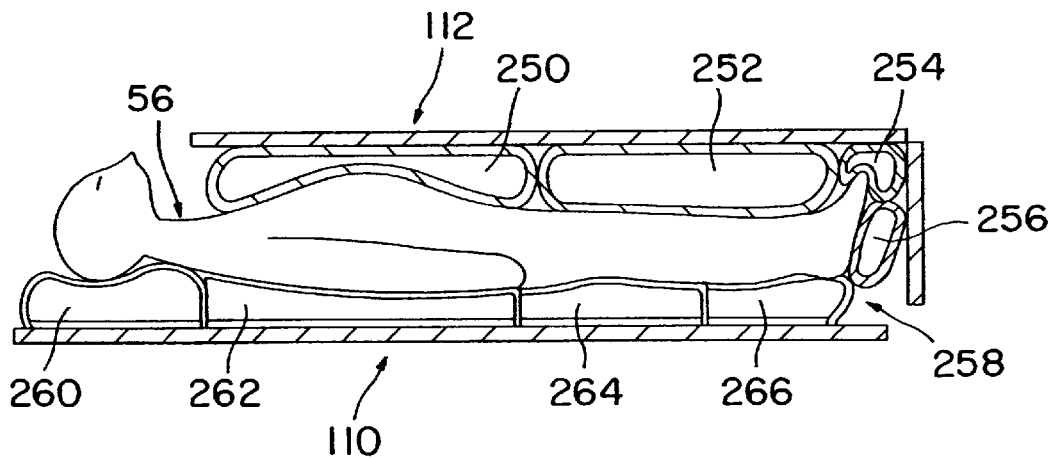
FIG. 19 is a sectional view illustrating a compression therapy apparatus of the present invention.

FIG. 19 illustrates an external chest compression device of the present invention. Illustratively, separate air cushions 250, 252, 254, 256 and 258 surround the patient 56 when the proning doors 172 and 174 are closed. The air cushions are all controlled separately. Each air cushion, 250, 252, 254, 256, and 258 may be divided into separate zones. For instance, zone 258 located below patient 56 may be divided into four separate zones 260, 262, 264 and 266 as indicated. Cushion 250 and a chest and abdomen zone 262 of lower air cushion 258 are increased in pressure to place the patient's chest cavity under varying amounts of external pressure. This may provide respiratory benefits to the patient 56, similar to prone positioning. Cushion 250 and chest and abdomen zone 262 of lower air cushion 258 may also be used to provide chest physiotherapy such as percussion or vibration therapy, either separately or together. Inflation and deflation of the cushions may also be synchronized to a patient's breathing pattern and then adjusted to wean the patient from a respirator. Cushions 252, 254, 256 and the leg and foot zones 264 and 266 of bottom cushion 258 are inflated simultaneously to provide deep vein thrombosis therapy. Inflation and deflation of all the zones is controlled by a blower coupled to a main controller of the bed 10. The controller of bed 10 can also be connected to various monitoring outputs from devices such as $SaO_2$, EKG, respiration, etc., and the pressure in the zones can be varied based upon outputs from these monitoring device outputs to synchronize treatment with the physical parameters detected. Interface pressure sensors may be included in each cushion to provide feedback to the controller.

Monitoring devices, such as a patient's blood oxygen level sensor $SaO_2$ monitoring systems are well known. The controller of the present invention is also used to control the frequency of rotation of the patient using feedback from a blood oxygen saturation monitor coupled to the patient. The processor determines whether the patient requires more or less frequent rotation based upon the blood oxygen saturation levels detected and either suggests the change in rotation frequency to the caregiver via a display or automatically adjusts the frequency of rotation of the patient support surface based on the blood oxygen saturation levels detected. The illustrated frequency is about 0.67 degrees per second. This frequency is adjusted based on the output of the blood oxygen saturation monitor.

A controller of the present invention is used to program various features of the bed to provide a sequence of treatments to the patient selected from a matrix of possible bed positions and therapies. The controller can provide continuous lateral rotation of the patient about longitudinal axis 38 at different angles and frequencies. The controller may be programmed to rotate the bed further to one side than to the other during the continuous lateral rotation. In addition, the controller can be programmed to provide head elevation, for example, at selected times. The controller can be coupled to various types of sensors, such as discussed above including sensors for measuring blood oxygen level, oxygen index, end tidialed $CO_2$, etc., to adjust the treatment or position of the patient based on outputs from these sensors.

Although the invention has been described in detail with reference to a certain illustrated embodiment, variations and modifications exist within the scope and spirit of the present invention as described and defined in the following claims.

What is claimed is:

1. A proning bed comprising:
  a frame;
  a first support member coupled to the frame and configured to be located adjacent a posterior side of a patient;
  a second support member coupled to the frame and configured to be located adjacent an anterior side of the pattern;
  a first patient support including an inflatable bladder, the first patient support supported by the first support member and configured to support the patient in a supine position:
  a second patient support supported by the second support member and configured to support the patient in a prone position; and
  wherein the first support member and the second support member are configured to rotate the first patient support and the second patient support about a longitudinal axis.

2. The proning bed of claim 1, further comprising a rotatable drive mechanism operably coupled to the first support member and the second support member, the drive mechanism being configured to rotate the first patient support and the second patient support about the longitudinal axis.

3. The proning bed of claim 2, wherein the drive mechanism is configured to rotate the first patient support and the second patient support by at least 180° about the longitudinal axis.

4. The proning bed of claim 1, wherein the second patient support includes an inflatable bladder.

5. The proning bed of claim 4, further comprising a controller configured to selectively inflate and deflate the inflatable bladder of the first patient support and the inflatable bladder of the second patient support.

6. The proning bed of claim 1, further comprising a fluid supply in fluid communication with the inflatable bladder of the first patient support and configured to inflate and deflate the bladder.

7. The proning bed of claim 1, wherein the first support member comprises at least one pivotable door configured to provide access to the patient in a prone position, the inflatable bladder being coupled to the at least one pivotable door.

8. The proning bed of claim 1, wherein the second support member comprises at least one pivot-able door configured to provide access to the patient in a supine position.

9. The pinning bed of claim 1, further comprising a backboard supported by the first support member, the backboard removably coupled to the proning bed and being configured to facilitate transport of the patient to and from the proning bed.

10. The proning bed of claim 9, wherein the backboard includes at least one air bladder configured to provide a pressure reducing surface for the patient.

11. The proning bad of claim 9, further comprising a plurality of connectors configured to mechanically couple the backboard to the proning bed.

12. A method for handling a patient on a proning bed, the method comprising:
  providing a proning bed having a bed support, first and second support members, and first and second patient supports coupled to the first and second support members, at least one of the first and second patient supports including an inflatable portion, and the patient supported by the first patient support in a supine position;
  coupling the first support member to the bed support;
  coupling the second support member to the bed support;
  positioning a patient on the first patient support in a supine position;
  inflating the inflatable portion; and
  moving the first support member and the second support member so that the patient is supported by the second patient support in a prone position.

13. The method of claim 12, wherein the first patient support includes an inflatable portion.

14. The method of claim 13, wherein the second patient support includes an inflatable portion.

15. The method of claim 14, wherein the proning bed further includes a fluid supply configured to selectively inflate and deflate the inflatable portions of the first and second patient supports.

16. The method of claim 14, further comprising the atop of inflating the inflatable portion of the second patient support before the first and second support members are moved.

17. The method of claim 13, wherein the step of inflating the inflatable portion comprises the step of inflating the inflatable portion of the first patient support.

18. The method of claim 17, further comprising the step of deflating the inflatable portion of the first patient support.

19. The method of claim 13, wherein the step of inflating the inflatable portion comprises the step of inflating the inflatable portion of the first patient support before the first patient support is coupled to the bed support.

20. The method of claim 12, further comprising the step of removing the first support member after the step of moving the first support member and the second support member.

21. The method of claim 12, further comprising the steps of transporting the patient to the proning bed on a backboard, and removably coupling the backboard to the bed support.

22. A therapy bed comprising:
a base;
a frame coupled to the base;
a patient support assembly including a first lateral side and a second lateral side, the patient support assembly coupled to the frame and configured to be rotated about a longitudinal axis the longitudinal axis being between the first lateral side and the second lateral side, the patient support assembly including a backboard having a first patient support surface, the backboard being removably coupled to the frame to facilitate transport of the patient to and from the therapy bed; and
a motorized drive mechanism configured to rotate the patient support assembly about the longitudinal axis.

23. The therapy bed of claim 22, further comprising a second patient support surface, the patient lying on the first patient support surface in a supine position, the first and second support surfaces configured to rotate by at least 180° about the longitudinal axis so that the patient Is lying on the second patient support surface in a prone position.

24. The therapy bed of claim 23, wherein the motorized drive mechanism is a rotatable drive mechanism.

25. The therapy bed of claim 23, further comprising a plurality of connectors configured to mechanically couple the backboard to the frame.

26. The therapy bed of claim 22, wherein the motorized drive mechanism includes a rotatable member coupled to the patient support assembly and a motor operably coupled to the rotatable member, the motor being configured to rotate the rotatable member.

27. The therapy bed of claim 22, further comprising a controller operably coupled to the motorized drive mechanism to control the rotation of the patient support assembly about the longitudinal axis.

28. The therapy bed of claim 27, wherein the controller is programmable.

29. The therapy bed of claim 28, wherein the controller is programmed to position the patient support assembly in a prone position.

30. The therapy bed of claim 28, further comprising a pivot mechanism coupled to the patient support assembly to rotate the patient support assembly about a pivot axis, the pivot axis being generally transverse to the longitudinal axis, the pivot mechanism being operably coupled to the controller.

31. The therapy bed of claim 30, wherein the controller is programmed to cause rotation of the patient support assembly about the pivot axis to provide rotational therapy to the patient.

32. A therapy bed comprising:
a base;
a frame coupled to the base; and
a patient support assembly coupled to the frame and configured to be rotated about a longitudinal axis, the patient support assembly including a backboard having a first patient support surface, the backboard being removably coupled to the frame to facilitate transport of the patient to and from the therapy bed, and wherein the backboard includes an inflatable portion.

33. The therapy bed of claim 32, wherein the inflatable portion of the backboard is deflated when the patient is in the prone position.

34. The therapy bed of claim 32, wherein the second patient support surface includes an inflatable portion.

35. The therapy bed of claim 34, wherein the inflatable portion of the second patient support surface is inflated when the patient is in the prone position.

36. The therapy bed of claim 34, further comprising a fluid supply configured to selectively inflate and deflate the inflatable portion of the backboard and the second support surface.

37. A method for handling a patient on a therapy bed, the method comprising the steps of:
providing a backboard including a first patient support surface;
positioning a patient on the first support surface in a supine position;
providing a therapy bed in spaced relation to the backboard, the therapy bed including a base and a frame coupled to the base;
transporting the backboard to the therapy bed;
releasably coupling the backboard to the frame;
providing a motorized drive mechanism to impart a rotation to the patient support surface; and
rotating the first patient support surface of the backboard about a longitudinal axis such that the patient is rotated from a supine position to a generally prone position.

38. The method of claim 37, further comprising the steps of providing a second patient support surface, coupling the second patient support surface to the frame, and simultaneously rotating the first patient support surface and the second patient support surface.

39. The method of claim 38, wherein the step of simultaneously rotating the first patient support surface and the second patient support surface comprises rotating the first patient support surface and the second patient support surface by at least 180° about the longitudinal axis.

40. The method of claim 38, further comprising the step of removing the backboard from the therapy bed after the step of rotating the first patient support surface and the second patient support surface.

41. The method of claim 37, wherein the step of releasably coupling comprises the step of mechanically coupling the backboard to the frame through a plurality of connectors.

42. The method of claim 37, further comprising the step of providing a controller operably coupled to the motorized drive mechanism and configured to control the motorized drive mechanism.

43. The method of claim 42, further comprising the step of automatically positioning the patient in the prone position.

44. A method for handling a patient on a therapy bed, the method comprising the steps of:
providing a backboard including a first patient support surface and an inflatable portion;
positioning a patient on the first support surface in a supine position;
providing a therapy bed in spaced relation to the backboard, the therapy bed including a base and a frame coupled to the base;

transporting the backboard to the therapy bed;

releasably coupling the backboard to the frame; and rotating the first patient support surface of the backboard about a longitudinal axis.

45. The method of claim 44, wherein the second patient support surface includes an inflatable portion.

46. The method of claim 44, further comprising the step of inflating the inflatable portion of the backboard.

47. The method of claim 46, wherein the inflating step is performed before the rotating step.

48. The method of claim 46, further comprising the step of deflating the inflatable portion of the backboard.

49. The method of claim 45, further comprising the step of inflating the inflatable portion of the second patient support surface.

50. The method of claim 45, wherein the therapy bed further includes a fluid supply configured to selectively inflate and deflate the inflatable portion of the backboard and the inflatable portion of the second patient support surface.

* * * * *